United States Patent
Huynh

(10) Patent No.: US 11,830,614 B2
(45) Date of Patent: Nov. 28, 2023

(54) METHOD AND SYSTEM FOR OPTIMIZING HEALTHCARE DELIVERY

(71) Applicant: Tran Tu Huynh, New York, NY (US)

(72) Inventor: Tran Tu Huynh, New York, NY (US)

(73) Assignee: Opticsurg, Inc., New York, NY (US)

( * ) Notice: Subject to any disclaimer, the term of this patent is extended or adjusted under 35 U.S.C. 154(b) by 0 days.

(21) Appl. No.: 15/677,030

(22) Filed: Aug. 15, 2017

(65) Prior Publication Data

US 2018/0268110 A1 Sep. 20, 2018

Related U.S. Application Data

(60) Provisional application No. 62/473,987, filed on Mar. 20, 2017.

(51) Int. Cl.
| | |
|---|---|
| G16H 40/67 | (2018.01) |
| G06F 16/44 | (2019.01) |
| G16H 10/40 | (2018.01) |
| G16H 30/20 | (2018.01) |
| H04N 23/60 | (2023.01) |
| H04N 23/69 | (2023.01) |

(Continued)

(52) U.S. Cl.
CPC ............ G16H 40/67 (2018.01); G06F 16/44 (2019.01); G16H 10/40 (2018.01); G16H 30/20 (2018.01); H04N 23/60 (2023.01); H04N 23/69 (2023.01); H04N 23/90 (2023.01); G06F 3/013 (2013.01); G06F 3/017 (2013.01); G06F 3/0482 (2013.01); G06F 3/167 (2013.01); H04N 23/62 (2023.01)

(58) Field of Classification Search
CPC ...................................................... G16H 30/20
USPC ........................................................ 705/2–3
See application file for complete search history.

(56) References Cited

U.S. PATENT DOCUMENTS

| | | |
|---|---|---|
| 2011/0047033 A1 | 2/2011 | Mahaffey et al. |
| 2013/0308827 A1 | 11/2013 | Dillavou et al. |

(Continued)

FOREIGN PATENT DOCUMENTS

| | | | | |
|---|---|---|---|---|
| WO | WO-2015164402 A1 * | 10/2015 | ............. | A61B 90/37 |

OTHER PUBLICATIONS

Takafumi Hiranaka et al., The use of smart glasses for surgical video streaming, 24 Surgical Innovation 151-154 (2017), https://journals.sagepub.com/doi/epub/10.1177/1553350616685431 (Year: 2017).*

*Primary Examiner* — Jonathon A. Szumny
*Assistant Examiner* — Nicholas Akogyeram, II
(74) *Attorney, Agent, or Firm* — POLSINELLI PC; Adam C. Rehm; Zachary D. Cleary

(57) ABSTRACT

A healthcare delivery system, a wearable computing device and a method are disclosed. The method includes capturing, by the wearable computing device worn by a medical practitioner, medical multimedia data of a patient during a medical procedure. The method further includes displaying one or more selectable options associated with the medical multimedia data on a display screen of the wearable computing device to the medical practitioner. Further, the method includes receiving a selection of a selectable option from among the one or more selectable options. Thereafter, at least one action is performed on the medical multimedia data based on the selection of the selectable option. An example of the at least one action includes sharing at least a part of the medical multimedia data with a third party device.

18 Claims, 9 Drawing Sheets

(51) Int. Cl.
*H04N 23/90* (2023.01)
*G06F 3/01* (2006.01)
*G06F 3/16* (2006.01)
*G06F 3/0482* (2013.01)
*H04N 23/62* (2023.01)

(56) References Cited

U.S. PATENT DOCUMENTS

| | | | |
|---|---|---|---|
| 2014/0071043 A1* | 3/2014 | Jung | G06F 3/03 |
| | | | 345/156 |
| 2014/0168056 A1* | 6/2014 | Swaminathan | G06F 3/147 |
| | | | 345/156 |
| 2014/0204190 A1* | 7/2014 | Rosenblatt, III | H04N 7/14 |
| | | | 348/77 |
| 2014/0222526 A1* | 8/2014 | Shakil | G16H 15/00 |
| | | | 705/7.38 |
| 2015/0088546 A1* | 3/2015 | Balram | G16H 10/60 |
| | | | 705/3 |
| 2015/0236859 A1 | 8/2015 | Gross | |
| 2016/0203265 A1* | 7/2016 | Hardie | G16H 40/63 |
| | | | 705/3 |
| 2017/0042631 A1* | 2/2017 | Doo | H04N 13/344 |
| 2017/0258526 A1 | 9/2017 | Lang | |
| 2018/0168780 A1* | 6/2018 | Kopelman | A61B 34/20 |
| 2020/0038120 A1* | 2/2020 | Ziraknejad | G06F 3/016 |

* cited by examiner

METHOD AND SYSTEM FOR OPTIMIZING HEALTHCARE DELIVERY

FIELD OF THE INVENTION

The present invention generally relates to healthcare technology and, more particularly, to a method and system for optimizing healthcare delivery using augmented reality technology.

BACKGROUND

Generally, healthcare refers to maintaining health via diagnosis, treatment, and prevention of disease. Healthcare delivery refers to providing healthcare services to people by organizations such as healthcare facilities/hospitals with the affiliation of health professionals such as doctors, surgeons, physicians and the like. Delivering healthcare is a complex and multi-pronged process. More specifically, treatment and diagnosis of diseases can be done via medical therapy and/or via multiple diagnostic modalities, interventional modalities, procedural modalities, surgical modalities and the like. In an example scenario, a surgeon may need to access medical imaging such as a Magnetic Resonance Imaging (MRI) scan of a patient to review essential anatomic information for pre-operative planning as well as navigation while in surgery. Such medical images can be difficult to visualize easily without an interruption to an on-going surgery/medical procedure. Further, it is not possible for the surgeon to use a mouse or keyboard, as they are unsterile and pose a risk of infection to view the medical images on an electronic device such as a desktop computer. In such scenarios, the surgeon may request his assistant to operate the desktop computer to retrieve the medical images or other information related to the patient. Moreover, if the image is not pre-stored on the desktop computer, the surgeon may have to hold the procedure until the required images are made available to him. Such manual coordination of collecting patient data is a time consuming process. Further, a lot of other resources of the healthcare facility such as the operating room, medical equipments, medical staff, special surgeons, etc. stay underutilized because of such manual management of the healthcare delivery. In addition, current medical image viewing equipments utilized in the healthcare facility are cumbersome, ergonomically unfriendly and bulky.

Therefore, there is a need to provide portability of the patient data including medical history for faster decision making during the medical procedure. There is a need to provide an optimized management of the healthcare delivery through the use of an augmented reality wearable computing device to facilitate a real time solution for accessing the medical data of the patient and sharing the data with a remote device.

SUMMARY

Various embodiments of the present invention provide a method and system for optimized healthcare delivery.

In an embodiment, a method includes capturing, by a wearable computing device worn by a medical practitioner, medical multimedia data of a patient during a medical procedure. The method further includes displaying one or more selectable options associated with the medical multimedia data on a display screen of the wearable computing device to the medical practitioner. Further, the method includes receiving a selection of a selectable option from among the one or more selectable options. Thereafter, the method includes performing at least one action on the medical multimedia data based on the selection of the selectable option. The at least one action includes sharing at least a part of the medical multimedia data with a third party device.

In another embodiment, a healthcare delivery system includes a wearable computing device and at least one server. The wearable computing device is worn by a medical practitioner. The wearable computing device is configured to capture medical multimedia data of a patient during a medical procedure and display one or more selectable options associated with the medical multimedia data on a display screen of the wearable computing device to the medical practitioner. The wearable computing device is also configured to receive a selection of a selectable option from among the one or more selectable options to perform at least one action on the medical multimedia data. The at least one server is in operative communication with the wearable device. The at least one server is configured to receive at least a part of the medical multimedia data from the wearable computing device, and facilitate provision of requisite data associated with the medical procedure to be displayed on the display screen of the wearable computing device.

In another embodiment, a wearable computing device is disclosed. The wearable computing device includes at least one camera configured to capture medical multimedia data of a patient during a medical procedure, and a display screen configured to display one or more selectable options associated with the medical multimedia data to the medical practitioner. The wearable computing device also includes a sensor assembly configured to interpret a selection of the one or more selectable options made by the medical practitioner, and a processing unit for performing at least one action on the medical multimedia data based on the selection interpreted by the one or more sensors. Further, the wearable computing device includes a communication module configured to communicate with a third party device for sharing at least a part of the medical multimedia data.

BRIEF DESCRIPTION OF THE FIGURES

For a more complete understanding of example embodiments of the present invention, reference is now made to the following descriptions taken in connection with the accompanying drawings in which.

The drawings referred to in this description are not to be understood as being drawn to scale except if specifically noted, and such drawings are only exemplary in nature.

DETAILED DESCRIPTION

The various aspects of the present invention are presented in terms of the embodiments, herein depicted in FIGS. 1 to 10. The embodiments are described herein for illustrative purposes and are subject to many variations. It is understood that various omissions and substitutions of equivalents are contemplated as circumstances may suggest or render expedient, but are intended to cover the application or implementation without departing from the spirit or the scope of the present invention. Further, it is to be understood that the phraseology and terminology employed herein are for the purpose of the description and should not be regarded as limiting. Any heading utilized within this description is for convenience only and has no legal or limiting effect. The terms "a" and "an" herein do not denote a limitation of quantity, but rather denote the presence of at least one of the referenced item, unless the context suggests otherwise.

Various embodiments of the present invention provide a method and system for optimizing healthcare delivery using augmented reality technology. In particular, the invention discloses an application-platform/interface that allows for utilization of a wearable augmented reality optical computing system (hereinafter referred to as "wearable computing device") for capturing medical multimedia data of a patient during a medical procedure. The wearable computing device helps surgeons with a portable and ergonomic dedicated screen and complete control of multimedia data manipulation specifically during an on-going medical procedure. Some non-exhaustive examples of medical multimedia data include medical history, laboratory test results, medical images (such as X-rays, CAT scans (Computed Axial Tomography), MRI scans, ultrasound etc.), medical video data associated with multiple visual modalities (including, but not limited to, laparoscopy, robotics, angiography, interventional radiologic procedures etc.), personal statistics like sex, age and weight, medication, allergies, immunization status etc. associated with a patient. Further, the invention allows for portably accessing the captured medical multimedia data within a shared network/private network in real time by touch free commands. Some embodiments facilitate sharing medical multimedia data with remote devices in real time. Other embodiments facilitate receiving multimedia data from the remote devices and displaying the same on the wearable computing device in real time. Various embodiments of the present invention facilitating optimized healthcare delivery are further explained with reference to FIGS. 1 to 10.

Figure 1:
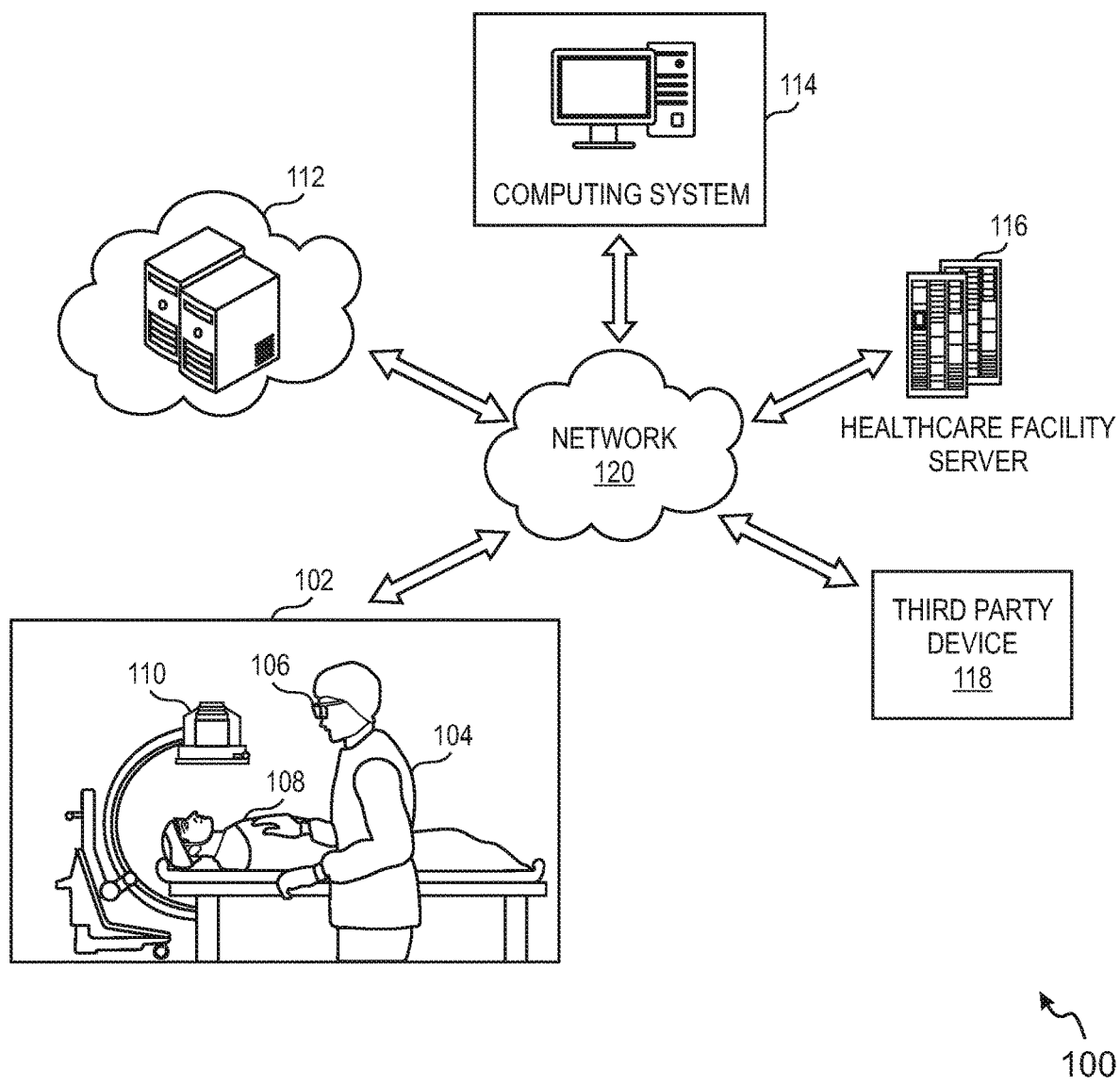
FIG. 1 illustrates an example environment incorporating a healthcare delivery system related to at least some embodiments of the present invention.

FIG. 1 illustrates an example environment related to at least some embodiments of the present invention. It should be understood, however, that the environment incorporating a healthcare delivery system 100 is illustrated and hereinafter described is merely illustrative of an arrangement for describing some example embodiments, and therefore, should not be taken to limit the scope of the embodiments. As such, it should be noted that at least some of the components described below in connection with the environment may be optional and thus in some example embodiments may include more, less or different components than those described in connection with the example embodiment of FIG. 1 or with subsequent FIGS. 2 to 10.

In the illustrated example representation, a healthcare facility 102 depicts a medical practitioner for example a surgeon (hereinafter interchangeably referred to as 'a surgeon 104') having worn a wearable computing device 106 (e.g., a pair of smartglasses) while performing a medical procedure on a patient 108 using a medical device 110. In an illustrative example, the surgeon 104 may be any of a general surgeon, an orthopedic surgeon, an oncologist or a surgical oncologist, a dental surgeon, an ophthalmic surgeon, a neurosurgeon, an interventional radiologist, an interventional cardiologist, a gastroenterologist, an angiologist, a hematologist, a neonatologist, an obstetrician, a plastic surgeon, a cardiovascular surgeon, an ENT surgeon, and the like. It should be noted that surgeon 104 is merely an example, and a nurse, a medical assistant, a medical staff representative, an anesthesiologist, an MRI or an X-Ray technician and the like may also perform the medical procedure. Further, the medical procedure may be any type of diagnostic procedure, therapeutic procedure, surgical procedure, emergency room procedure, interventional procedure or bedside procedure being performed on the patient 108.

The medical procedure may be of capturing medical images associated with the patient 108. Medical imaging is a type of diagnostic or therapeutic modality that creates visual representations of the interior of a body for clinical analysis and medical intervention, as well as visual representation of the function of organs or tissues. Some non-exhaustive examples include radiography/fluoroscopy, tomography, MRI, endovascular, ultrasound, endoscopy, laparoscopy and the like. Various medical procedures include capturing medical video data associated with multiple visual modalities (including, but not limited to, laparoscopy, robotics, angiography, interventional radiologic procedures etc). Accordingly, the medical device 110 may correspond to specific medical procedure being performed on the patient 108. In various embodiments, the wearable computing device 106/smartglasses 106 can be any wearable augmented reality computing device/system such as, but not limited to, Google Glass® or Microsoft HoloLens® headsets or any other similar head-mounted display device.

The healthcare delivery system 100 is further shown depicting a communication network such as a network 120 that connects the wearable computing device 106 (hereinafter alternatively referred to as "smartglasses 106") to at least one server and a plurality of entities such as third party devices. Some examples of the at least one server may be a server system 112, a computing system 114, and a healthcare facility server 116. In an example embodiment, the server system 112, the computing system 114, and the healthcare facility server 116 may be a single composite server, or each of them may have multiple sub-systems. An example of the third party device is shown as a third party device 118. The network 120 may be a centralized network or may include a plurality of sub-networks that may offer a direct or indirect communication between the entities. For example, the network 120 may include wired networks, wireless networks and combinations thereof. Some non-limiting examples of the wired networks may include Ethernet, local area networks (LANs), fiber-optic networks, and the like. Some non-limiting examples of the wireless networks may include cellular networks like GSM/3G/4G/5G/LTE/CDMA networks, wireless LANs, Bluetooth, Wi-Fi or ZigBee networks, and the like. An example of the combination of wired and wireless networks may include the Internet.

The server system 112 may correspond to a Web-based platform (for example, a cloud platform) capable of being accessed over the network 120. In other example embodiments, a remote plug-in that uses cloud based APIs (Application Program Interfaces) may be utilized to connect and extract the information from the server system 112. The Web-based platform may provision a healthcare delivery application service as a Web service accessible through a Website. In such a scenario, a plurality of surgeons, doctors, medical staff members, nurses, assistant doctors, medical students, patients, caretakers of the patients and the like (hereinafter collectively referred to as end-users/users) may access the Website over the network 120 using Web browser applications installed in their respective electronic devices and thereafter use the services of the application.

The server system 112 may also be configured to store a healthcare delivery application program and provision instances of the application to the end-users for facilitating optimized healthcare delivery by provisioning medical multimedia data associated with the patient in real time. The end-users may request the server system 112 to access the healthcare delivery application over the network 120 using their respective electronic devices. The instances of the application may thereafter be downloaded on respective electronic devices (such as the smartglasses 106, the third party device 118 and the computing system 114) of the end-users in response to their request for accessing the application. Alternatively, in some embodiments, the application may be factory installed within the electronic devices (such as the wearable computing device 106) associated with the end-users and, as such, the users may not need to explicitly request the application from the server system 112. Alternatively, the application may be requested by the end-users (such as the medical staff or the surgeons) using their electronic devices from the healthcare facility server 116 which may further communicate with the server system 112 for accessing the application. It is understood that the healthcare facility server 116 is configured to facilitate a private network for the healthcare facility 102.

In one embodiment, a user upon accessing the Website and/or the healthcare delivery application associated with the server system 112 may be presented with one or more User Interfaces (UI) capable of facilitating a plurality of options for user selection related to medical multimedia data extraction of the patient 108. One such exemplary UI is explained later with reference to FIG. 7.

In an embodiment, the smartglasses 106 are configured to capture medical multimedia data (hereinafter referred to as data/patient data) associated with the patient 108 during the on-going medical procedure. The captured data is sent to the server system 112 over the network 120. The server system 112 is configured to process the data and to cause display of the data on a display screen of the smartglasses 106. The server system 112 is further configured to send the data to other devices of the healthcare delivery system 100. For example, the data may be sent to the third party device 118 associated with end-users. Some non-exhaustive examples of the third party device 118 include cellular phones, tablet computers, laptops, mobile computers, personal digital assistants (PDAs), mobile televisions, mobile digital assistants, smartglasses, or any other types of communication or multimedia devices. The third party device 118 may be synced or paired with the smartglasses 106 in order to send and receive various types of data. It is understood that there may be present a plurality of third party devices for communicating with the smartglasses 106.

In one example embodiment, the smartglasses 106 are configured to send the captured data of the patient 108 to the computing system 114 over the network 120 for transforming non-compatible data and/or non-compatible third party devices to be compatible for use on the smartglasses 106. This is applicable only in scenarios when the smartglasses 106 do not have required processing power and/or dedicated programs installed therein to run different types of medical multimedia data. Compatibility is broadly defined as the ability to utilize the medical multimedia data visual modalities with the smartglasses 106 via the installation of healthcare delivery application upon powering up the smartglasses 106 and syncing/pairing the desired third party devices. The computing system 114 is configured to include increased robust processing power, operating memory, and connection with external devices/modalities in order to facilitate interfacing between the smartglasses 106 and the non-compatible third party devices/data. In one example embodiment, the computing system 114 can act as an extension of the smartglasses 106 as an interface to allow processing, sharing, and saving of the medical multimedia data of the patient 108. In one embodiment, the computing system 114 may generate a request to the server system 112 for transforming non-compatible medical multimedia data into compatible medical multimedia data. The server system 112 may include necessary program instructions for transformation. Post-transformation, the server system 112 may provision display of the transformed non-compatible medical multimedia data on the display screen of the smartglasses 106 directly or send it back to the computing system 114 for display.

It should be noted that the sever system 112 may be external to the healthcare facility 102, or the server system 112 can be entirely embodied in any of the computing system 114 and the healthcare facility server 116. Further, the computing system 114 can be embodied in the healthcare facility server 116.

Figure 2:
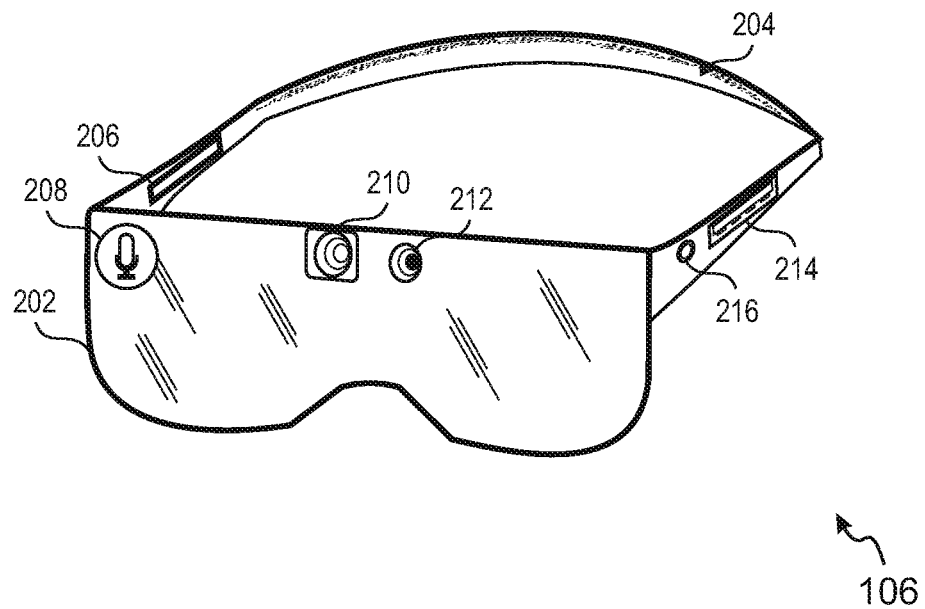
FIG. 2 illustrates an example representation of a wearable computing device, in accordance with an example embodiment of the present invention.

FIG. 2 illustrates an example representation of the wearable computing device 106/smartglasses 106, in accordance with an example embodiment of the present invention. The smartglasses 106 include a headband 204 connected to a display screen 202. The headband 204 may be adjustable for a comfortable and secure fit. The headband 204 includes a communication module 206 and an Input/Output (I/O) port (see, 216). In various embodiments, the I/O port 216 may include such as a USB port or an earphone/speaker connector port or a power charging port. For example, the speaker connector port may be used to provide verbal cues to the user or can be used to communicate with a person remotely. The USB port 214 may be used for connecting external devices such as the computing system 114 or the third party device 118 for data transfer and other such purposes.

In an example embodiment, the display screen 202 may be transparent 3D (three dimensional) lenses. The lenses may be formed of any material that can suitably display a projected image or graphic. The lenses may facilitate an augmented reality or heads-up display where a projected image or graphic is superimposed over a real-world view as perceived by the user through the lenses. In another example embodiment, the images and other information may be projected on the user's retina, or displayed on the user's contact lenses. In an example embodiment, the smartglasses 106 may include a built in processing unit 214 and batteries for processing power (not shown). In one embodiment, the processing unit 214 may include required processing power for transforming non-compatible data into compatible data for properly viewing them on the display screen 202 of the smartglasses 106 without the need of sending the non-compatible data to the computing system 114 or to the server system 112 for performing the transformation.

The smartglasses 106 further include a front facing sensor and depth camera assembly 210 (hereinafter referred to as a sensor assembly 210) for capturing user movements, position tracking and touch free commands via motion. Some non-exhaustive examples of the sensor may include a gyroscope, an accelerometer, a compass and the like. Additionally, a finger-operated touchpad (not shown) may be provided on any part such as the headband 204 of the smartglasses 106. The finger-operable touch pad may be used by a user to provide input commands. The sensor assembly 210, along with the processing unit 214, is configured to act to interpret gazes and hand movements of the user as input commands (for example, a selection of one or more selectable options displayed on the display screen 202). In scenarios of on-going medical procedures, it may be more convenient for the user being the surgeon 104 to manipulate the multimedia data via the sensor assembly 210. For instance, the surgeon 104 can move, pinch and rotate his or her fingers similar to the movement used to operate Smartphone or tablets, and such gestures can be interpreted by the sensor assembly 210. The sensor assembly 210 can detect these movements in space through the use of the forward facing depth camera and other sensors, which would allow for touch free use of the smartglasses 106 that would not only be convenient and efficient, but would also maintain sterility in an operating room of the healthcare facility 102. Further, dedicated eye-movements to perform dedicated tasks may be programmed. For example, the smartglasses 106 may capture an image based on receiving an input command of wink and may turn the display screen 202 on when eyes are focused on the display screen 202 for a pre-defined time period.

The smartglasses 106 are further depicted to include a front facing camera 212 (hereinafter referred to as camera 212) to capture what the user (such as the surgeon 104) sees. The camera 212 records and shares real time endeavors. The input commands for turning on the camera 212 may be provided by speaking, swiping on the display screen 202, clicking a button, or using one or more gestures. In other embodiments, the camera 212 may be provided on other parts of the smartglasses 106. The camera 212 may be configured to capture images or record videos at various resolutions or at different frame rates. In an example embodiment, there may be provided multiple cameras, and each may be configured to capture different views. In at least one embodiment, the forward-facing image captured by the camera 212 may be used to generate an augmented reality where computer generated images appear to interact with the real-world view perceived by the user. The camera 212 is configurable to zoom in on a desired area to display on the display screen 202. Zooming can be accomplished using gestures or other input commands. In one embodiment, there is also provided a microphone 208 for receiving voice commands and recording sounds/speech as needed. In an embodiment, the user may be enabled to customize or change what information/options/tasks are displayed and when they are displayed using various input commands such as voice command, gestures, through a predefined user profile and the like.

The captured medical multimedia data and associated UIs are displayed on the display screen 202, and the surgeon 104 can perform various actions based on the selections made in the UI displayed on the display screen 202. The selections can be made by the surgeon 104 by providing multiple forms of inputs. Some examples of these inputs may include gesture inputs, voice commands, touch based inputs, press of a mechanical button, or gaze input. Such inputs can be interpreted by the sensor assembly 210 in operative communication with the processing unit 214. Some non-exhaustive examples of the actions include performing zoom-in/zoom-out of the display, sharing a part of the medical multimedia data with the at least one server (112, 114 or 116), or the third party device 118, requesting requisite data needed for the medical procedure from the third party device 118 or the at least one server (112, 114 or 116), storing the medical multimedia data in a storage location, etc. Some example representation of selection inputs and associated actions are described with reference to FIGS. 3 to 7.

The communication module 206 is configured to facilitate communication (for example, receive, send or share data) of the smartglasses 106 to the server system 112, the computing system 114 and the third party device 118 associated with the user. The communication module 206 is configured to cause display of one or more UIs on the electronic devices, thereby enabling the user to view/retrieve medical multimedia data of the patients. The communication module 206 may further be configured to send non-compatible data from the smartglasses 106 to the computing system 114 for transforming them into compatible data for properly viewing them on the display screen 202 of the smartglasses 106. The communication may be achieved over a communication network, such as the network 120. In at least one example embodiment, the communication module 206 may provide Wi-Fi and Bluetooth capability to the smartglasses 106 to allow wireless connections with other devices. Such capability allows the user to save, recall, and share the data through a private network that can be created at each healthcare facility (such as hospital, urgent care or the healthcare facility 102) by using dedicated servers such as the healthcare facility server 116 of FIG. 1.

In an example scenario of minimally invasive surgeries, a doctor is required to use several forms of guidance simultaneously, while looking back-and-forth between the surgical equipment being used and real-time images on a screen of a computer. Instead, the images from guidance devices or software may be directly displayed onto the doctor's smartglasses by removing the tedious need to use additional screens and making procedures quicker and safer. Alternatively, if a nurse wants to know measurement of a depth of a wound using the smartglasses, she may point her finger on wound. The camera 212 may capture an image or record a video of the wound as necessary based on detection of pointed finger and/or a voice command received from the nurse such as "Measure depth of the wound". The captured image/video may be sent to the server system 112 which may provide appropriate result on the smartglasses being used by the nurse such as "The wound is two centimeters deep." The output may be provided in text format or voice format.

Figure 3:
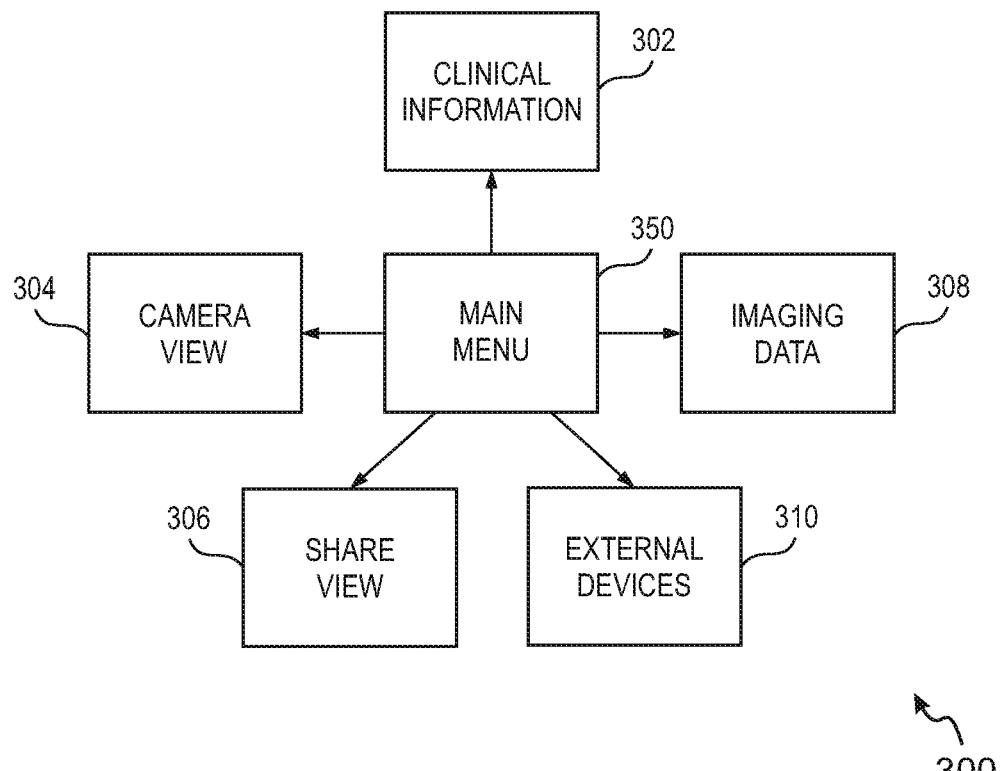
FIG. 3 illustrates a block diagram representation of a plurality of options facilitated for a user selection on a display screen of the wearable computing device, in accordance with an example embodiment of the present invention.

FIG. 3 illustrates a block diagram representation 300 of a plurality of options facilitated for a user selection on the display screen 202 of the wearable computing device 106, in accordance with an example embodiment of the present invention. As shown, the plurality of options are represented by boxes 350, 302, 304, 306, 308 and 310. In an embodiment, as the smartglasses 106 (with or without the computing system 114) is turned ON, the healthcare delivery application is activated and one or more API calls are made to the server system 112 to cause display of the box 350 with text "Main Menu" for user selection on the display screen 202 of the smartglasses 106. From the "Main Menu", the user can navigate via touch free commands that could be a combination of gaze, hand gestures, and voice commands. As shown in the representation 300, upon receiving user selection of "Main Menu", the UI may display one or more options for user selection such as, but not limited to the box 320 with text "Clinical Information", the box 304 with text "Camera View", the box 306 with text "Share view", the box 308 with text "Imaging Data" and the box 310 with text "External Devices".

In one example embodiment, when a user selection corresponding to "Clinical Information" (box 302) is received, the server system 112 is configured to perform corresponding action for example transmitting data/information related to the patient to be displayed through one or more UIs on the display screen 202 of the smartglasses 106. In an embodiment, this data may have been previously saved onto the smartglasses 106 directly, or through the computing system 114, or on the privately shared network facilitated by the healthcare facility server 116 inside the healthcare facility 102. The information displayed may include, for example, the patient's profile and a diagnosis profile. The patient's profile may further include his/her name, birth date, a medical record number, chief complaint, gender and the like. The diagnosis profile may include previous and current diagnoses, previous and current medications, patient preferences and the like.

In one example embodiment, when the user selection of "Camera View" (box 304) is received, the camera 212 embedded in the smartglasses 106 is enabled to capture images and videos. The image and videos may be stored in the local storage space of the smartglasses 106 or they may be sent to the server system 112 or the computing system 114 for external storage and later retrieval. More features of "Camera View" are explained later in detail with reference to FIG. 5.

In an example embodiment, when the user selection of "Share View" (box 306) is received, the communication module 206 is enabled to perform corresponding action for example sharing the recording videos or capturing images with the server system 112, the computing system 114 or the third party device 118. Such medical multimedia data can be shared with one or more compatible third party devices. For example, in a scenario where multiple smartglasses are being used by a plurality of surgeons during a medical procedure, one of the surgeons may be designated with administrative rights to share his live camera view with other compatible smartglasses being used by the remaining surgeons. The administrative rights may also allow the smartglasses to take photographs and video recording of the camera view while sharing the live view simultaneously. In one embodiment, this information is then accessible instantaneously via "Clinical Information" (box 302).

In one embodiment, when the user selection of "Imaging Data" (box 308) is received, a two dimensional (2D) or a three dimensional (3D) view may be represented to the user through one of the UIs on the display screen 202. In another example embodiment, patient specific stored imaging data (as would be provided when "Imaging Data" is selected by the user) may alternatively be accessed via the "Clinical Information" (box 302). In an example embodiment, when the surgeon using the smartglasses 106 enters an operating room, the patient's clinical information (such as notes, images, videos etc.) may be automatically displayed on the display screen 202 in anticipation of the surgical time-out and pre-operative checklists.

In yet another embodiment, when user selection of "External Devices" (box 310) is selected, one or more compatible external devices/third party devices are provisioned on the display screen 202. In an embodiment, the external devices (such as the third party device 118, the computing system 114 of the FIG. 1) can be synced/paired with the smartglasses 106 to communicate with the smartglasses 106. Upon selection of the desired external device/third party device, the smartglasses 106 and the selected third party device may communicate with each other in real time. For example, a tablet associated with a medical student in a remote location may be enabled to receive live video from the smartglasses 106 being used by a physician during an on-going medical procedure for educational purposes. A simplified representation of a UI displaying medical multimedia data of a patient on the display screen 202 of the smartglasses 106 is explained later in detail with reference to FIG. 7.

Figure 4:
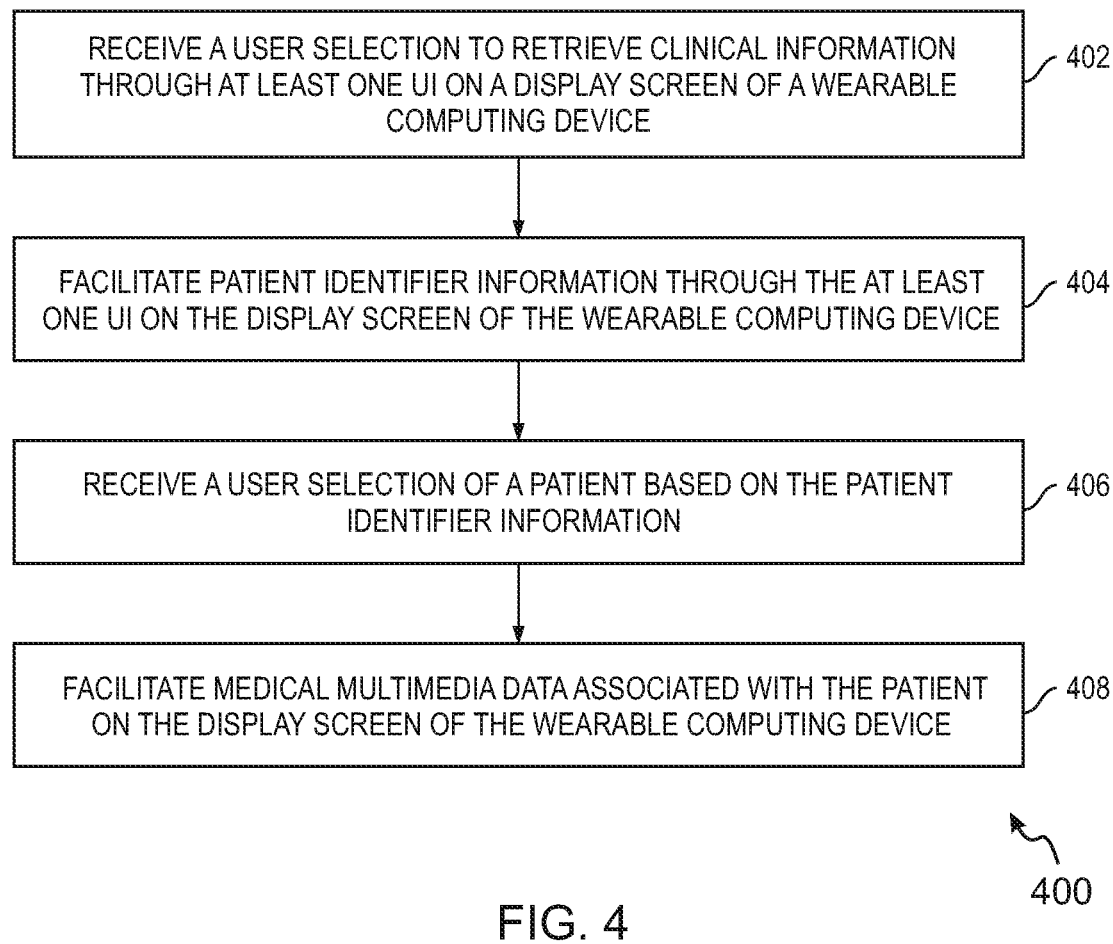
FIG. 4 illustrates an exemplary flow diagram depicting a method for retrieving medical multimedia data of a patient, in accordance with an example embodiment of the present invention.

FIG. 4 illustrates an exemplary flow diagram depicting method 400 for retrieving medical multimedia data of a patient, in accordance with an example embodiment of the present invention. The various steps and/or operations of the flow diagram, and combinations of steps/operations in the flow diagram, may be implemented by, for example, hardware, firmware, a processor, circuitry of at least one of the smartglasses 106, the server system 112, the computing system 114 of the present invention and/or by a different device associated with the execution of software that includes one or more computer program instructions.

At 402, a user selection to retrieve clinical information is received through at least one UI on a display screen of a wearable computing device. A user may provide gesture based or voice based commands to the wearable computing device (such as the smartglasses 106) for retrieving the clinical information using the UI on the display screen (such as the display screen 202).

At 404, patient identifier information is facilitated through the at least one UI on the display screen of the wearable computing device. The patient identification information includes such as, but not limited to, last name, first name, date of birth, medical record number, gender, age, etc., of a plurality of patients as recorded therein. In one embodiment, the user may be enabled to enter identification information of a desired patient by using various input commands to retrieve associated clinical information. In another example embodiment, unique identification information associated with each patient from among the plurality of patients may be displayed through the UI for user selection.

At 406, a user selection of a patient is received based on the patient identifier information.

At 408, medical multimedia data associated with the patient are facilitated on the display screen of the wearable computing device. Based on the user selection of relevant/desired patient, the server system 112 (or the computing system 114 or the healthcare facility server 116) is configured to review the associated medical multimedia information/data stored in a database accessible to the server system 112 (or the computing system 114 or the healthcare facility server 116). The medical multimedia data may include, such as, but not limited to notes, documents, laboratory reports, medical imaging data, recorded video files, physiological parameters, adverse condition predictions, tasks to be performed by the caretaker of the patient (such as the patient 108) upon discharge and the like. These options can be accessed concurrently via a multi-windows capability through at least one UI on the display screen of the wearable computing device. In an embodiment, a user selection to view stored notes or documents would display the desired documents associated with the relevant patient. In a similar manner, the user selection to view stored laboratory reports would display the desired laboratory reports (such as blood reports). Further, user selection to view stored imaging data would display the stored imaging data (such as X-rays). The note, documents, imaging data and laboratory reports can be left open, closed, reopened, and accessed once or repeatedly. In one embodiment, clinical information may be referred to as the medical multimedia data of the patient.

Figure 5:
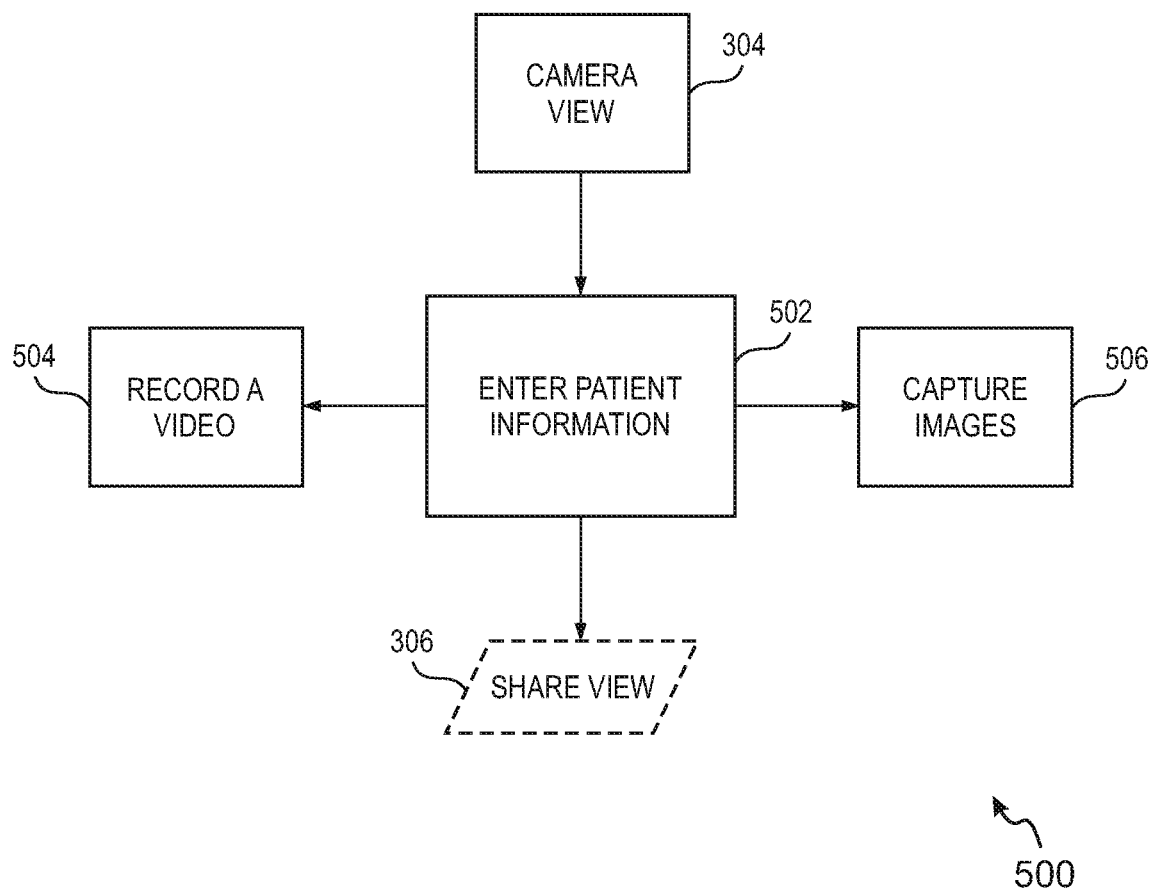
FIG. 5 illustrates a block diagram representation of a plurality of options facilitated on the display screen of the wearable computing device based on user selection of camera view, in accordance with an example embodiment of the present invention.

FIG. 5 illustrates a block diagram representation 500 of a plurality of options facilitated on the display screen 202 of the wearable computing device 106 based on the user selection of "Camera View" (box 304 of FIG. 3), in accordance with an example embodiment of the present invention. In an embodiment, based on the user selection of "Camera View" (box 304), the camera 212 is turned on and the user is provided with a plurality of options as represented by boxes 502, 504, 506 and 306. In an example embodiment, the box 502 with text "Enter Patient Information" may be provisioned to request a user to enter information related to a patient. The information could include last name, first name, date of birth, medical record number, gender, age, date of procedure/study, and time of procedure/study. The information can be inputted via the virtual keyboard and/or voice commands. In an example embodiment, the user may be enabled to bypass entering of patient information and directed to options as provisioned by the boxes 306, 504 and 506.

The box 504 with text "Record a Video" and the box 506 with text "Capture Images" allow user to record a video of an on-going medical procedure and capture images respectively. An example may be recording and capturing important or pertinent aspects and findings of the procedures to be utilized later as baseline information for the purposes of diagnosis, treatment, discussion, consultation, and ultimately optimizing the healthcare delivery. In another example scenario of an interaction/consultation with a patient, the clinicians/physicians/surgeons can record entire consultations with the patient and revisit the recorded footage at any time later, thereby providing patients with their full attention. Such facilitation prevents the clinicians from the worry of forgetting details of the interaction or procedure, taking paper based notes about the patient and maintaining file records of the notes and helps in reducing the time spent between consultations and allowing clinicians to spend more time with each patient.

In one embodiment, the captured data (audio, video, images, and patient information) may be stored on local storage space of the smartglasses 106, external memory of the computing system 114, storage modules of the healthcare facility server 116 or the database of the server system 112. In an example embodiment, the camera 212 is able to record and analyze pictures/images of the patient's face during a consultation to have patient's medical data displayed on the display screen 202 of the smartglasses 106. This type of photo recognition is most utilized in an emergency room (ER), where a large number of patients are being seen in a short period of time.

In another embodiment, an option to select "Share View" (box 306) may optionally be facilitated to the user upon selection of "Camera View" (box 304). As explained with reference to FIG. 3, the user selection of "Share View" would facilitate sharing of medical multimedia data with other compatible external devices/smartglasses being used by one or more different users. In one embodiment, the "Share View" option may be configured to always continue to function even if the user continues to capture multimedia data of the patient. For example, during medical procedures that have limited space and vantage points, a primary practitioner may need hands on assisting and therefore needs to share view for the assistant so that the procedure can progress safely and efficiently. In another example, when a trainee/assistant doctor encounters an issue during a medical procedure, generally, most of the data discussion occurs by telephone with superior doctor. The superior doctor is unable to access the data that the trainee sees, which is where the video conferencing of smartglasses 106 has a greater potential for sharing data, evaluating the trainee's performance and successfully advising the trainee to perform the medical procedure remotely.

Figure 6:
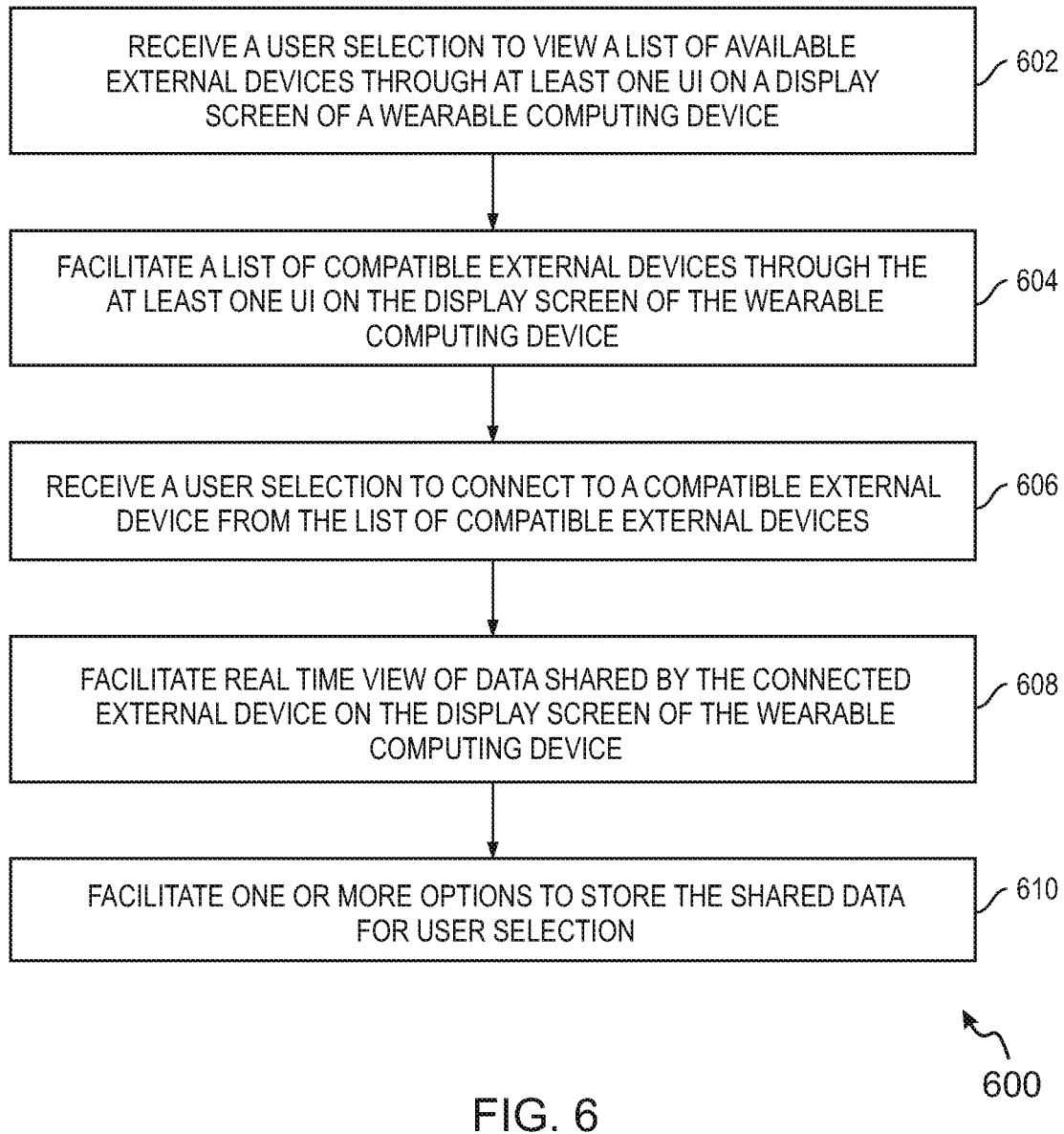
FIG. 6 illustrates a flow diagram depicting a method for facilitating communication with an external device, in accordance with an example embodiment of the present invention.

FIG. 6 illustrates a flow diagram depicting method 600 for facilitating communication with an external device, in accordance with an example embodiment of the present invention. it is noted that external device and third party device are interchangeably used throughout the description without deviating from the scope. The various steps and/or operations of the flow diagram, and combinations of steps/operations in the flow diagram, may be implemented by, for example, hardware, firmware, a processor, circuitry and/or by the smartglasses 106 or the server system 112 or the computing system 114 of the present invention and/or by a different device associated with the execution of software that includes one or more computer program instructions.

At 602, a user selection to view a list of available external devices is received through at least one UI on a display screen of a wearable computing device. A user may provide gesture based or voice based commands to the wearable computing device (such as the smartglasses 106) for retrieving the list of available external devices using the UI on the display screen (such as the display screen 202).

At 604, a list of compatible external devices is facilitated through the at least one UI on the display screen of the wearable computing device. If an external device is not compatible with the wearable computing device, the computing system 114 is used to process the external device data and make it compatible to be used with the wearable computing device. Alternatively, the external device may install the healthcare delivery application for resolving compatibility related issues. When an external device is paired/synced using the healthcare delivery application, such a device is shown on the display screen of the wearable computing device as compatible external device.

At 606, a user selection to connect to a compatible external device is received from the list of compatible external devices.

At 608, real time view of data shared by the connected external device is facilitated on the display screen of the wearable computing device. For example, a pathologist may be able to share requisite data, for example laboratory results, of a patient using his device (such as the third party device 118) to a wearable computing device being used by a doctor.

At 610, one or more options to store the shared data are facilitated for user selection. For example, the user can capture images or record video of the live display being shared by the external device and save the data in a database. The stored data can be accessed instantaneously via the user selection of "Clinical Information" (box 302 of FIG. 3).

Figure 7:
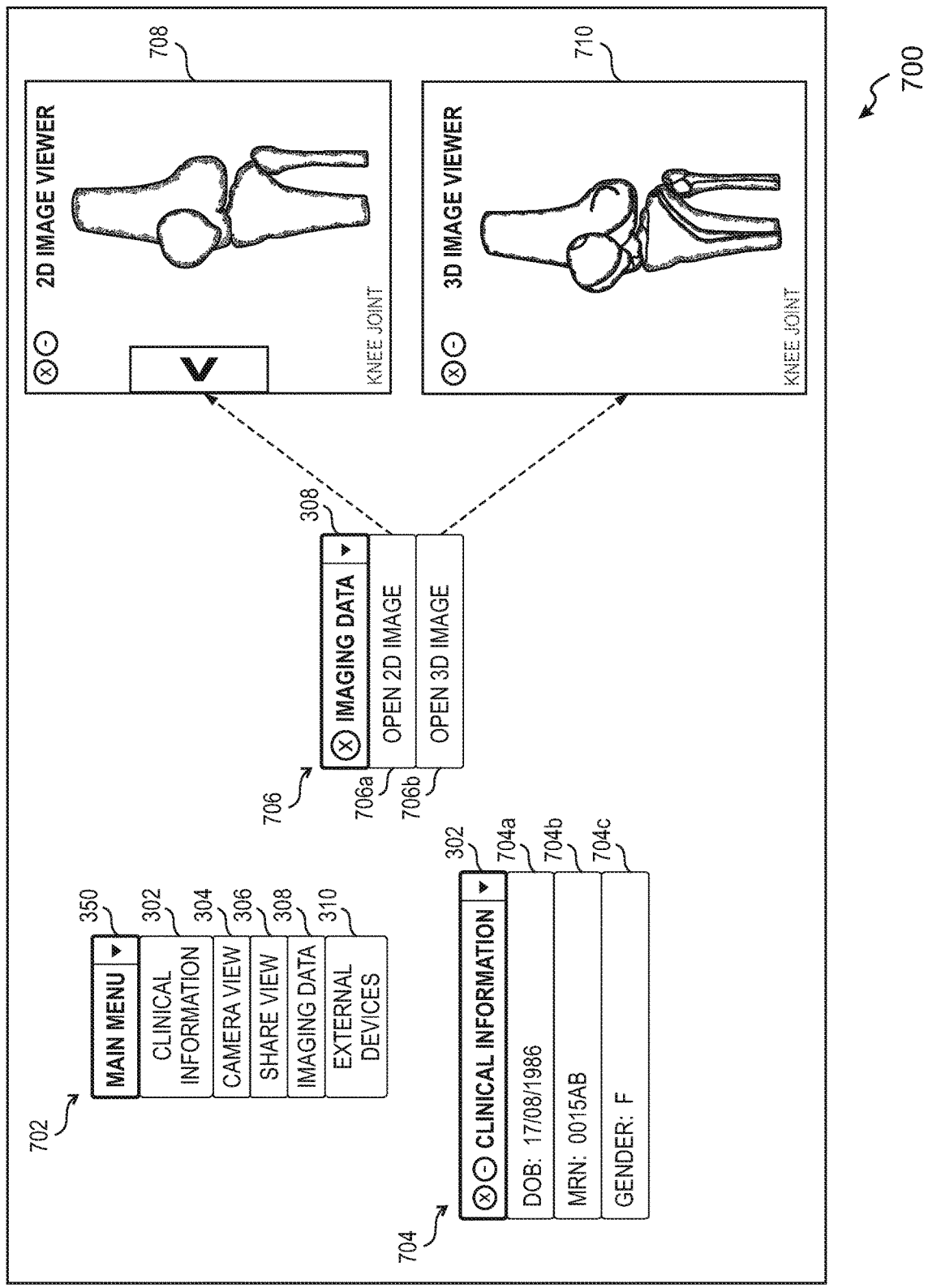
FIG. 7 illustrates a simplified representation of a User Interface (UI) displaying medical multimedia data of a patient on the display screen of the wearable computing device, in accordance with an example embodiment of the present invention.

FIG. 7 illustrates a simplified representation of a User Interface (UI) 700 displaying medical multimedia data of a patient on the display screen 202 of the wearable computing device 106/smartglasses 106, in accordance with an example embodiment of the present invention. As shown, the UI 700 is configured to display a plurality of windows such as 702, 704, 706, 708, and 710 on the display screen 202 of the smartglasses 106. It is noted that the healthcare delivery application platform may include several UIs in addition to the UI 700.

A window/widget 702 is depicted to include "Main Menu" (box 350) with a drop-down arrow depicted to further display boxes 302-310 respectively representing "Clinical Information", "Camera View", "Share View", "Imaging Data" and "External Devices" capable of receiving user selection. Use selection/input commands may be provided in various possible ways such as a voice command, a gaze command, a gesture command and the like. When "Clinical Information" (box 302) is selected by the user, a widget 704 may be displayed to the user using the UI 700 on the display screen 202 of the smartglasses 106. In the illustrated example representation, the window 704 includes identification information related to a patient via boxes 704a, 704b and 704c respectively showing "DOB" (Date of birth), "MRN" (Medical Reference Number) and "Gender" of the patient. In other examples, additional information such as profile picture, name, address etc. of the patient may also be displayed. Functions associated with the boxes 304-310 of the window 702 are not repeated again herein as they are explained in detail with reference to FIGS. 3, 5 and 6 and may similarly be displayed in a multi-windows representation as explained with reference to UI 700.

The UI 700 is further depicted to display a window/widget 706 with a drop-down arrow to display options for user selection to view medical images of a patient (such as the patient 108) in 2D or 3D format. For instance, when a user selection of "Open 2D Image" (box 706a) is received a corresponding 2D image of the patient may be displayed as directed by a dashed arrow in a window 708. The window 708 exemplarily displays a 2D image view of a knee joint of a patient. Similarly, when user selection of "Open 3D Image" (box 706b) is received, a corresponding 3D image in a new window 710 may be displayed. The window 710 exemplarily displays 3D image view of the knee joint shown in the window 708. In an embodiment, compartmentalization of the captured data is facilitated by the computing system 114 or the server system 112. For example, the data corresponding to different visual modalities may be clubbed together based on their types and then saved into the database of the computing system 114 or the server system 112. Further, the data can be clubbed together based on the date of capture. In an example embodiment, the multi-windows capability as explained with reference to UI 700 allows for keeping "Clinical Information" (box 302) to be always present using the widget 704, while utilizing other options such that saved multimedia data may be played back on the smartglasses 106 instantaneously based on user request.

In at least one example embodiment, the provisioning of the plurality of options at any time based on input commands corresponding to any of the widgets/windows explained above may cause one or more application programming interface (API) calls to the computing system 114 or to the server system 112 (shown in FIG. 1). In an embodiment, the computing system 114 (or the server system 112) may associate a Hyperlink Text Markup Language (HTML) tag or a JavaScript tag with the windows (702-710), which may be activated upon receiving an input command from the user. The activation of the tag may be configured to generate API calls to the computing system 114 (or the server system 112). The API calls may be embodied in form of a data signal capable of being securely transmitted over a communication network, such as the network 120. The computing system 114 or the server system 112, upon receiving such a communication, may be configured to cause display of one or more UIs capable of showing medical multimedia data of a patient and enabling the user to further select the medical multimedia data for viewing, storing and sharing with third party devices. The display of such a UI may be effected in substantially real-time (for example, on the order of milliseconds) subsequent to the provisioning of a user selection received corresponding to any widget/window.

Figure 8:
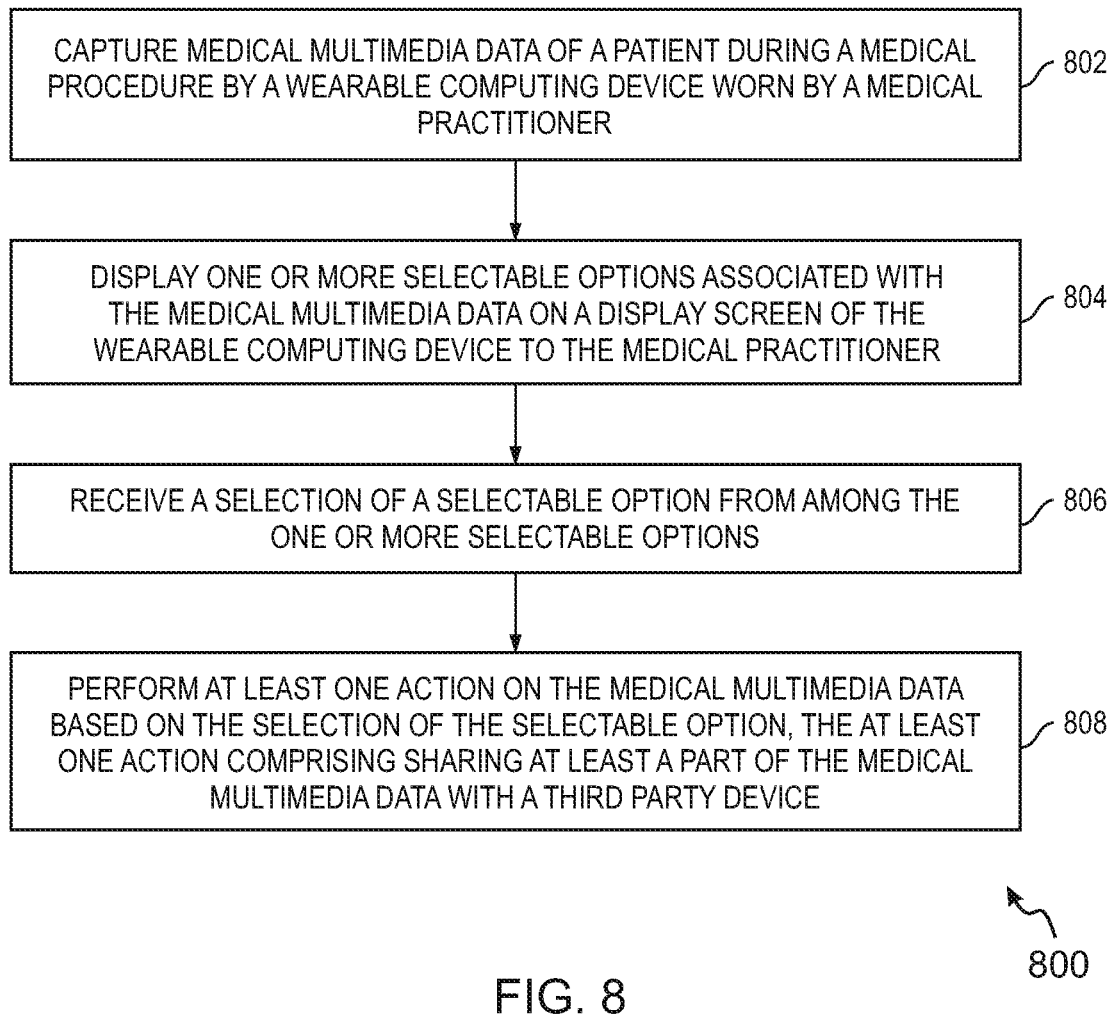
FIG. 8 illustrates yet another flow diagram depicting a method for facilitating optimized healthcare delivery, in accordance with an example embodiment of the present invention.

FIG. 8 illustrates yet another flow diagram depicting a method 800 for facilitating optimized healthcare delivery, in accordance with an example embodiment of the present invention. The various steps and/or operations of the flow diagram, and combinations of steps/operations in the flow diagram, may be implemented by, for example, hardware, firmware, a processor, circuitry and/or by the server system 112 or by the smartglasses 106, or by the computing system 114 or the healthcare facility server 116 of the present invention and/or by a different device associated with the execution of software that includes one or more computer program instructions. It should be noted that to facilitate discussions of the flowchart of FIG. 8, certain operations are described herein as constituting distinct steps performed in a certain order. Such implementations are examples only and non-limiting in scope. Certain operations may be grouped together and performed in a single operation, and certain operations can be performed in an order that differs from the order employed in the examples set forth herein. Moreover, certain or all operations of the methods 800 are performed in an automated fashion. These operations involve substantially no interaction with the user. These operations may involve interaction with the user via one or more user interface presentations.

At 802, medical multimedia data of a patient during a medical procedure is captured by a wearable computing device worn by a medical practitioner.

At 804, one or more selectable options associated with the medical multimedia data are displayed on a display screen of the wearable computing device to the medical practitioner. In an embodiment, one or more selectable options for user selection through the at least one UI on the display screen of the wearable computing device are facilitated to the medical practitioner.

At 806, a selection of a selectable option from among the one or more selectable options is received. The selection can be made by the medical practitioner using many forms of inputs such as gesture inputs, voice bases inputs or gaze inputs.

At 808, at least one action on the medical multimedia data is performed based on the selection of the selectable option. The at least one action includes sharing at least a part of the medical multimedia data with a third party device. In one embodiment, communication of the wearable computing device with a plurality of third party devices is facilitated. The plurality of third party devices may include a compatible third party device and a non-compatible third party device.

Figure 9:
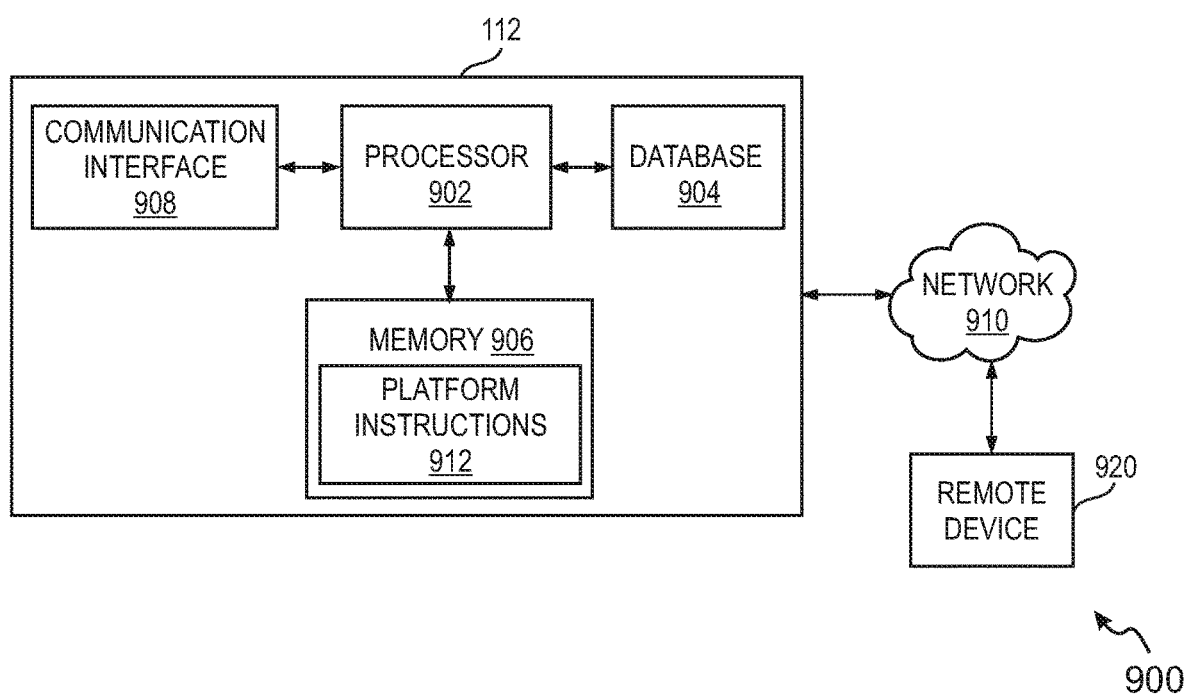
FIG. 9 illustrates a block diagram representation of a server system capable of implementing at least some embodiments of the present invention.

FIG. 9 illustrates a block diagram representation of the server system 112 or the healthcare facility server 116 or the computer system 114 capable of implementing the various embodiments of the present invention. The server system 112 includes at least one processor such as a processor 902, a database 904, at least one memory such as a memory 906, and a communication interface 908. The processor 902 is communicably coupled with the database 904, the memory 906 and the communication interface 908. In at least one embodiment, the server system 112 may be accessible to remote devices, such as the remote device 920, through a communication network, such as the network 910. It is understood that the server system 112 may include fewer or more components than those depicted in FIG. 9 without deviating from the scope of the invention.

In an embodiment, the memory 906 can be embodied as a part of the processor 902. The memory 906 includes machine executable instructions, hereinafter referred to as platform instructions 912. In various embodiments, the memory 906 is a storage device embodied as one or more volatile memory devices, one or more non-volatile memory devices, and/or a combination of one or more volatile memory devices and non-volatile memory devices, for storing micro-contents information and instructions. The memory 906 may be embodied as magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash ROM, RAM (random access memory), etc.).

Further, the processor 902 is capable of executing the platform instructions 912 stored in the memory 906 for performing one or more operations. It is understood that the processor 902 can be configured in a variety of ways. For example, the processor 902 may be embodied as a multi-core processor, a single core processor, or a combination of one or more multi-core processors and one or more single core processors. For example, the processor 902 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like.

The processor 902 may be configured to include one or more algorithms such as speech recognition algorithms, face recognition algorithms (e.g. for identifying the patient), natural language processing algorithms, and one or more dedicated algorithms/program instructions to convert/transform non-compatible third party devices/external devices into compatible third party devices for use with the smartglasses 106. The processor 902 is further configured to include specific program instructions for converting non-compatible medical multimedia data from various modalities into compatible version for use with the smartglasses 106. The processor 902 in conjunction with the communication interface 908 is configured to cause display of one or more UIs to facilitate the medical multimedia data of a patient during a medical procedure on the display screen of an electronic device associated with a user such as the remote device 920. The processor 902 is further configured to share live and/or previously stored data of a patient to the remote device 920. For example, the processor 902 is configured to send information stored in the database 904 such as, but not limited to, textual or graphical data from journal articles, clinical studies, treatment guidelines, equipment instructions, procedure checklists, or any other relevant medical or technical data to the remote device 920 associated with the user (such as the surgeon 104 or the medical staff representative or the medical student). The processor 902 is further configured to receive data from the remote device 920 and store in the database 904 for later retrieval. Further, the processor 902 is configured to facilitate various features for replaying the previously recorded videos such as FF (fast forward), RW (rewind), high-speed playback and the like.

The communication interface 908 is configured to facilitate communication between the server system 112 and the remote device 920. The communication may be achieved over a communication network, such as the network 910. In one embodiment, the communication interface 908 includes a transceiver for wirelessly communicating information to, or receiving information from, the remote device 920 (such as smartglasses 106, the computing system 114, the third party device 118, and the healthcare facility server 116) or other suitable display device, and/or another type of remote processing device. In another embodiment, the communication interface 908 is capable of facilitating operative communication with the remote devices and a cloud server using API (Application Program Interface) calls. Such communication may be achieved over a communication network, such as the network 910.

The database 904 may be any computer-operated hardware suitable for storing and/or retrieving data, such as, but not limited to storing the clinical information of patients, other medical multimedia data associated with the patients, list of external devices compatible to be used with the smartglasses 106 and the like. In various embodiments, the database 904 may include multiple storage units such as hard disks and/or solid-state disks in a redundant array of inexpensive disks (RAID) configuration. The database 904 may include a storage area network (SAN) and/or a network attached storage (NAS) system. In some embodiments, the database 904 may be integrated within a computer system such as the computer system 114 (as shown in FIG. 1). For example, computer system may include one or more hard disk drives as database 904. In other embodiments, database 904 may be external to a computer system and may be accessed by the computer system using a storage interface. The storage interface is any component capable of providing processor 902 with access to the database 904. The storage interface may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 902 with access to the database 904.

Figure 10:
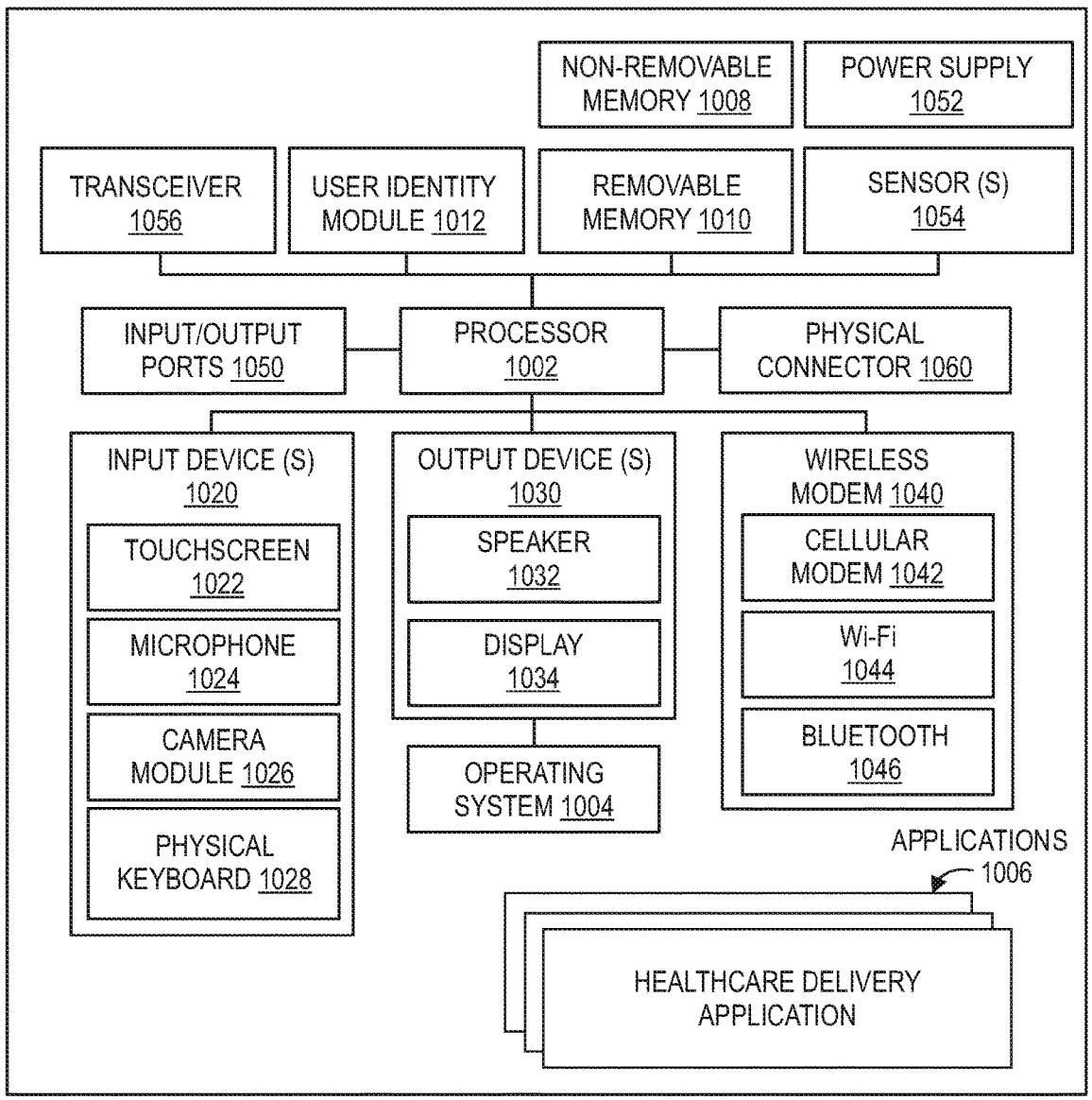
FIG. 10 illustrates an electronic device capable of implementing at least some embodiments of the present invention.

FIG. 10 illustrates an electronic device 1000 capable of implementing the various embodiments of the present invention. In an embodiment, the various operations performed by the server system 112 may be implemented using an application in an electronic device, such as the electronic device 1000. An example of the electronic device can be the computing system 114 or even the wearable computing device 106. For example, the electronic device 1000 may correspond to an electronic device associated with a user, such as for example, a surgeon, a medical staff representative, and the like. The electronic device 1000 is depicted to include one or more applications 1006, including a healthcare delivery application, which serves as an instance of the application downloaded from the server system 112 and capable of communicating through API calls with the server system 112 to facilitate optimized healthcare delivery.

It should be understood that the electronic device 1000 as illustrated and hereinafter described is merely illustrative of one type of device and should not be taken to limit the scope of the embodiments. As such, it should be appreciated that at least some of the components described below in connection with that the electronic device 1000 may be optional and thus in an example embodiment may include more, less or different components than those described in connection with the example embodiment of the FIG. 10. As such, among other examples, that the electronic device 1000 could be any of a mobile electronic devices, for example, a heads-up display system, a head-mounted device, a wearable computing device/smartglasses, cellular phones, tablet computers, laptops, mobile computers, personal digital assistants (PDAs), mobile televisions, mobile digital assistants, or any combination of the aforementioned, and other types of communication or multimedia devices. The electronic device 1000 may be to acquire, store, compute, process, communicate and/or display information such as audio, images, videos and text related to the patient. For example, the electronic device 1000 is incorporated with glasses to capture/send/receive/display information. In another example embodiment, the electronic device 1000 is a desktop computer configured for receiving/sending information from/to a receiver/transmitter as well as receiving input from a remote device.

The illustrated electronic device 1000 includes a controller or a processor 1002 (e.g., a signal processor, microprocessor, ASIC, or other control and processing logic circuitry) for performing such tasks as signal coding, data processing, image processing, input/output processing, power control, and/or other functions. An operating system 1004 controls the allocation and usage of the components of the electronic device 1000 and support for one or more applications programs (see, applications 1006), such as healthcare delivery application, that implements one or more of the innovative features described herein. In addition to healthcare delivery application, the applications 1006 may include common mobile computing applications (e.g., telephony applications, email applications, calendars, contact managers, web browsers, messaging applications) or any other computing application. The healthcare delivery application, in at least one example embodiment, may be configured to provide the logic to display/retrieve/share relevant medical multimedia data of a patient during a medical procedure, as explained with reference to FIGS. 1 to 9.

The illustrated electronic device 1000 includes one or more memory components, for example, a non-removable memory 1008 and/or removable memory 1010. The non-removable memory 1008 and/or removable memory 1010 may be collectively known as database in an embodiment. The non-removable memory 1008 can include RAM, ROM, flash memory, a hard disk, or other well-known memory storage technologies. The removable memory 1010 can include flash memory, smart cards, or a Subscriber Identity Module (SIM). The one or more memory components can be used for storing data and/or code for running the operating system 1004 and the applications 1006. The computing device 1000 may further include a user identity module (UIM) 1012. The UIM 1012 may be a memory device having a processor built in. The UIM 1012 may include, for example, a subscriber identity module (SIM), a universal integrated circuit card (UICC), a universal subscriber identity module (USIM), a removable user identity module (R-UIM), or any other smart card. The UIM 1012 typically stores information elements related to a mobile subscriber. The UIM 1012 in form of the SIM card is well known in Global System for Mobile Communications (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 1000 can support one or more input devices 1020 and one or more output devices 1030. The input devices 1020 and the output devices 1030 configure the input/output (I/O) module for the electronic device 1000. Examples of the input devices 1020 may include, but are not limited to, a touch screen/a display screen 1022 (e.g., capable of capturing finger tap inputs, finger gesture inputs, multi-finger tap inputs, multi-finger gesture inputs, or keystroke inputs from a virtual keyboard or keypad), a microphone 1024 (e.g., capable of capturing voice input), a camera module 1026 (e.g., capable of capturing still picture images and/or video images) and a physical keyboard 1028. Examples of the output devices 1030 may include, but are not limited to a speaker 1032 and a display 1034. Other possible output devices can include piezoelectric or other haptic output devices. Some devices can serve more than one input/output function. For example, the touch screen 1022 and the display 1034 can be combined into a single input/output device.

A wireless modem 1040 can be coupled to one or more antennas (not shown in the FIG. 10) and can support two-way communications between the processor 1002 and external devices, as is well understood in the art. The wireless modem 1040 is shown generically and can include, for example, a cellular modem 1042 for communicating at long range with the mobile communication network, a Wi-Fi compatible modem 1044 for communicating at short range with an external Bluetooth-equipped device or a local wireless data network or router, and/or a Bluetooth-compatible modem 1046. The wireless modem 1040 is typically configured for communication with one or more cellular networks, such as a GSM network for data and voice communications within a single cellular network, between cellular networks, or between the electronic device 1000 and a public switched telephone network (PSTN). The wireless modem 1040 may in at least one example embodiment configure the communication module of the electronic device 1000.

The electronic device 1000 can further include one or more input/output ports 1050, a power supply 1052, one or more sensors 1054 for example, an accelerometer, a gyroscope, a compass, or an infrared proximity sensor for detecting the orientation or motion of the electronic device 1000, a transceiver 1056 (for wirelessly transmitting analog or digital signals) and/or a physical connector 1060, which can be a USB port, IEEE 1294 (FireWire) port, and/or RS-232 port. The illustrated components are not required or all-inclusive, as any of the components shown can be deleted and other components can be added.

Various embodiments of the present invention provide a method and system for facilitating optimized healthcare delivery using augmented reality technology. Features of the present invention improve patient care, increase efficiency, and decrease healthcare costs thereby optimizing healthcare delivery. The application-platform/interface of the present invention allows utilization of wearable augmented reality optical computing system for sharing protected data via private network, accessing protected data within a shared network, recording/sharing of real time data, providing touch free commands, instant data availability, including portable and ergonomic usage. In particular, the invention is directed towards optimizing health care delivery related to surgical procedures, interventional procedures, diagnostic procedures and bedside procedures by optimizing access and utilization of multimedia data in a portable/wearable fashion. The invention discloses an approach for providing direct access to various modalities of medical imaging data via an application platform that is usable with the smartglasses. Various features of the present invention may be utilized under a variety of different situations. For example, a patient may capture an image of his MRI scan using his electronic device and send it to his doctor for getting a quick review of the scan. The doctor may see the image on the smartglasses and reply to the patient by voice/video conferencing using the smartglasses without having to allot a dedicated consultation appointment. Moreover, the image scan can be sent to an EMR recorder by the doctor using the smartglasses for keeping the up-to-date records of the patient. Further, the various features of the invention may be used for medical education where a student or a group of students may be enabled to view an on-going surgery as being explained by the surgeon in real time from remote location.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

The methods or processes explained with references to the foregoing Figures may be executed by, for example, components of the server system 112 (of FIG. 9). Particularly, the server system 112 its various components, such as the processor 902, the database 904, the memory 906 and the communication interface 908 may be enabled using software and/or using transistors, logic gates, and electrical circuits (for example, integrated circuit circuitry such as ASIC circuitry). Various embodiments of the invention may include one or more computer programs stored or otherwise embodied on a computer-readable medium, wherein the computer programs are configured to cause a processor or computer to perform one or more operations (for example, operations explained herein with reference to FIG. 4, FIG. 6 and FIG. 8). A computer-readable medium storing, embodying, or encoded with a computer program, or similar language, may be embodied as a tangible data storage device storing one or more software programs that are configured to cause a processor or computer to perform one or more operations. Such operations may be, for example, any of the steps or operations described herein. In some embodiments, the computer programs may be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash memory, RAM (random access memory), etc.). Additionally, a tangible data storage device may be embodied as one or more volatile memory devices, one or more non-volatile memory devices, and/or a combination of one or more volatile memory devices and non-volatile memory devices. In some embodiments, the computer programs may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

What is claimed is:

1. A method comprising:
   capturing, by at least one camera of smartglasses worn by a medical practitioner, medical multimedia data of a patient during a medical procedure, the smartglasses including a display screen, a sensor, and a processor, the display screen including a transparent lens;
   using a facial recognition algorithm via the processor to:
      identify the patient based on the medical multimedia data,
      retrieve previously collected patient data associated with the patient from a database accessible to the smartglasses, and
      cause the display screen to display the previously collected patient data;
   receiving, via the processor, a customization user input customizing which selectable options are displayed;
   displaying, via the display screen and at least partly using a user profile based on the customization user input, a plurality of selectable options superimposed over a real-world view of the medical practitioner through the transparent lens of the display screen;
   receiving, via the sensor, a selection by the medical practitioner of one of the plurality of selectable options, the selection enabling real-time communication with a particular external device;

requesting data, via the processor, from the particular external device based on the selection, the data requested by the medical practitioner for the medical procedure;

receiving the data, via the smartglasses, from the particular external device associated with the selection in response to the requesting of the data, the data received by the smartglasses including at least a portion created in real time based on the real-time communication and sent by the particular external device, wherein the portion of the data created in real time is a result of a measurement of a depth of a wound on the patient based on an image or video of the wound captured by the smartglasses and sent to the particular external device, the image or video of the wound being captured in response to detection of a gesture by a user of the smartglasses referring to the wound; and displaying, via the display screen, the data received from the particular external device during the medical procedure.

2. The method of claim 1, wherein the sensor is configured to receive the selection by the medical practitioner by receiving at least one of a gesture input, a voice input, or a gaze input.

3. The method of claim 1, further comprising:
communicating with at least one server to cause at least a portion of the medical multimedia data to be processed.

4. The method of claim 1, further comprising:
storing the medical multimedia data in a database accessible to the smartglasses.

5. The method of claim 4, wherein the medical multimedia data comprises at least one of medical history of the patient, laboratory test results, medical images, or medical video data associated with a plurality of visual modalities.

6. The method of claim 1, wherein the portion of the data created in real time is created by a user of the particular external device.

7. A healthcare delivery system comprising:
smartglasses operable to be worn by a medical practitioner, the smartglasses including at least one camera, a display screen, a sensor, and a processor, the display screen including a transparent lens, the smartglasses configured to:
capture, via the at least one camera, medical multimedia data of a patient during a medical procedure,
use a facial recognition algorithm via the processor to:
identify the patient based on the medical multimedia data,
retrieve previously collected patient data associated with the patient from a database accessible to the smartglasses, and
cause the display screen to display the previously collected patient data;
display, via the display screen, a plurality of selectable options superimposed over a real-world view of the medical practitioner through the transparent lens, each of the plurality of selectable options directed to a different device of a plurality of external devices paired with the smartglasses, the smartglasses configured for data sharing with each of the plurality of external devices according to the plurality of selectable options,
receive, via the sensor, a selection by the medical practitioner of an option from among the plurality of selectable options, the selection enabling real-time communication with a particular external device of the plurality of external devices,
request data, via the processor, from the particular external device based on the selection, the data requested by the medical practitioner for the medical procedure, and
display, via the display screen, the data received from the particular external device associated with the selection in response to the request by the medical practitioner, the data superimposed over the real-world view of the medical practitioner through the transparent lens of the display screen; and
at least one server in communication with the smartglasses, the at least one server configured to:
receive at least a part of the medical multimedia data from the smartglasses,
receive the data from the particular external device, the data received from the particular external device including at least a portion created in real time based on the real-time communication, and in response to detection of a gesture by a user of the smartglasses, and
facilitate the display of the data superimposed over the real-world view of the medical practitioner through the transparent lens of the display screen by transforming the data from non-compatible multimedia data into compatible multimedia data for the display screen.

8. The healthcare delivery system of claim 7, wherein the sensor is configured to receive the selection by the medical practitioner via at least one of a gesture input, a voice input, or a gaze input.

9. The healthcare delivery system of claim 7,
wherein,
the at least one camera is operable to capture the medical multimedia data, and
the medical multimedia data includes one or more images or videos.

10. The healthcare delivery system of claim 7, further comprising:
a database for storing the medical multimedia data.

11. The healthcare delivery system of claim 7, wherein the plurality of external devices include a plurality of healthcare system devices and at least one third party device.

12. The healthcare delivery system of claim 11, wherein the data is guidance data for the medical procedure.

13. The healthcare delivery system of claim 7,
wherein,
the smartglasses include an eye-movement algorithm stored via a memory component,
the eye-movement algorithm is configured to be implemented by the processor, and
the smartglasses are configured to:
receive, via the sensor, a dedicated eye-movement by the medical practitioner,
interpret, via the processor, the dedicated eye-movement as an input command to execute a dedicated task, and
execute, via the processor, the dedicated task in response to the input command.

14. Smartglasses comprising:
at least one camera configured to capture medical multimedia data of a patient during a medical procedure being performed by a medical practitioner;
a display screen including a transparent lens, the display screen configured to display a plurality of selectable options superimposed over a real-world view of the medical practitioner through the transparent lens, each of the plurality of selectable options directed to a different device of a plurality of external devices paired with the smartglasses, the smartglasses configured for data sharing with each of the plurality of external devices according to the plurality of selectable options;

a sensor assembly configured to interpret a selection of one of the plurality of selectable options made by the medical practitioner, the selection enabling real-time communication with a particular external device of the plurality of external devices; and a processor configured to (i) request data for the medical procedure from the particular external device based on the selection made by the medical practitioner, (ii) cause at least a part of the medical multimedia data to be shared with the particular external device, and (iii) receive the data from the particular external device responsive to the selection made by the medical practitioner, the data received from the particular external device including at least a portion created in real time based on the real-time communication, wherein the portion of the data created in real time is a result of a measurement of a depth of a wound on the patient based on an image or video of the wound captured by the smartglasses and sent to the particular external device, the image or video of the wound being captured in response to detection of a gesture by a user of the smartglasses referring to the wound, wherein the processor is configured to implement a facial recognition algorithm to:

identify the patient using the medical multimedia data, retrieve previously collected patient data associated with the patient from a database accessible to the smartglasses, detect a first dedicated eye movement by detecting, with the sensor assembly a wink gesture by the medical practitioner, capture an image using the at least one camera using the wink gesture as an input command, detect a second dedicated eye movement by determining eyes of the medical practitioner are focused on the display screen for a predefined amount of time, turn on the display screen responsive to the eyes of the medical practitioner being focused on the display screen for the predefined amount of time, and cause the display screen to display the previously collected patient data.

15. The smartglasses of claim 14, wherein the processor is configured to transform the data to enable display of the data on the display screen.

16. The smartglasses of claim 14, wherein the sensor assembly is configured to interpret an input made by the medical practitioner as the selection.

17. The smartglasses of claim 14, wherein the plurality of external devices include a plurality of healthcare system devices and at least one third party device.

18. The smartglasses of claim 17, wherein the data is guidance data for the medical procedure.

* * * * *